United States Patent

Kayasato et al.

[11] Patent Number: 5,908,955
[45] Date of Patent: Jun. 1, 1999

[54] PROCESS FOR PRODUCING ALKYL 3-AMINO-4-SUBSTITUTED BENZOATES

[75] Inventors: Jun-ichi Kayasato; Shingo Sato, both of Kanagawa, Japan

[73] Assignees: Sankio Chemical Co., Ltd., Tokyo; Fuji Photo Film Co., Ltd., Minami Ashigara, both of Japan

[21] Appl. No.: 09/000,716

[22] Filed: Dec. 30, 1997

[30] Foreign Application Priority Data

Jan. 14, 1997 [JP] Japan .................................. 9-004660

[51] Int. Cl.⁶ .................................................. C07C 229/00
[52] U.S. Cl. ............................................. 560/45; 560/47
[58] Field of Search ........................................ 560/45, 47

[56] References Cited

U.S. PATENT DOCUMENTS 3,725,072  4/1973  Yoshida et al. .
4,135,050  1/1979  Hess et al. ............................... 560/19

*Primary Examiner*—Brian M. Burn
*Assistant Examiner*—Brian J. Davis
*Attorney, Agent, or Firm*—Burns, Doane, Swecker & Mathis, LLP

[57] ABSTRACT

A process for producing an alkyl 3-amino-4-substituted benzoate represented by the following formula (II) is described, in which a 3-amino-4-substituted benzoic acid or an alkali metal salt thereof represented by the following formula (I) is allowed to react with an alkyl halide in the presence of a basic carbonate:

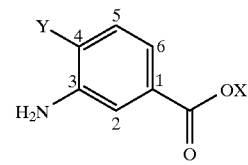

(I)

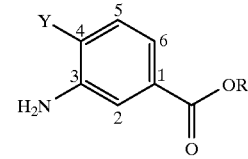

(II)

wherein R represents an alkyl group, X represents an alkali metal atom or a hydrogen atom, and Y represents an alkoxy group or a halogen atom.

9 Claims, No Drawings

PROCESS FOR PRODUCING ALKYL 3-AMINO-4-SUBSTITUTED BENZOATES

FIELD OF THE INVENTION

The present invention provides a process for producing alkyl 3-amino-4-substituted benzoates of high purity in high yields by a simple procedure, the benzoates being useful as intermediates for silver halide photographic materials and others.

BACKGROUND OF THE INVENTION

A process for the synthesis of alkyl 3-amino-4-substituted benzoates has hitherto been investigated, in which alkyl esters derived from a 3-nitro-4-substituted benzoic acid undergo amination through reduction. However, when catalytic reduction is applied to a 3-nitro-4-halogenobenzoic acid, the active halogen atom adjacent to the nitro group of the acid is liable to be eliminated, which makes it difficult to produce the desired products in high yields. Although a conventional procedure of reduction in which iron powder is used ensures formation of the desired products from a 3-nitro-4-alkoxy-benzoic acid, the procedure requires complicated operations such as disposal of the iron powder. As a result, the esterification of a commercially readily available 3-amino-4-substituted benzoic acid by the Fischer method has been attempted. However, in the esterification, alkylation of the amino group also simultaneously takes place to give the desired products only in low yields.

SUMMARY OF THE INVENTION

An object of the present invention is to provide a novel process for producing, without causing such problems, alkyl 3-amino-4-substituted benzoates of high purity in high yields by a simple procedure.

As a result of intensive studies, the present inventors have found that the object can be finally attained by introducing a novel process as described below:

A process for producing alkyl 3-amino-4-substituted benzoates represented by the following formula (II), in which a 3-amino-4-substituted benzoic acid or an alkali metal salt thereof represented by the following formula (I) is allowed to react with an alkyl halide in the presence of a basic carbonate:

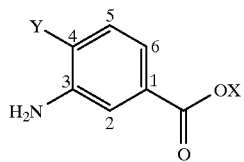

(I)

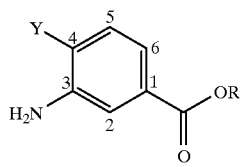

(II)

wherein R represents an alkyl group, X represents an alkali metal atom or a hydrogen atom, and Y represents an alkoxy group or a halogen atom.

R represents an unsubstituted or substituted alkyl group having, preferably 6 to 18 carbon atoms, more preferably 10 to 16 carbon atoms.

Although this process can be applied to the introduction of common unsubstituted or substituted alkyl groups, it is particularly effective for introduction of long-chain alkyl groups. Examples of the alkyl groups include an aliphatic alkyl group such as a decyl group, a dodecyl group, a tetradecyl group and a hexadecyl group; a cyclic alkyl group such as a 2-ethylcyclohexyl group and a cyclohexylmethyl group; an alkoxycarbonylalkyl group such as a decyloxycarbonylmethyl group, a dodecyloxycarbonylmethyl group, a 1-octyloxycarbonylethyl group, a 1-decyloxycarbonylethyl group and a 1-dodecyloxycarbonylethyl group; and an alkylaminocarbonylalkyl group such as a dodecylaminocarbonylmethyl group and an N-methyl-N-dodecylaminocarbonylmethyl group. Preferred examples of the alkyl groups include a decyl group, a dodecyl group, a tetradecyl group and a 1-dodecyloxycarbonylethyl group. These alkyl groups may be straight chain, or branched.

Further, preferred examples of the alkyl halides include alkyl bromides, and alkyl chlorides.

In the formula (I) or (II) as given above, X represents a hydrogen atom, or an alkali metal atom such as sodium, and potassium, preferably a hydrogen atom or sodium, and more preferably a hydrogen atom. Y represents a halogen atom such as chlorine, bromine and fluorine or an alkoxy group having 1 to 18 carbon atoms, preferably an alkoxy group having 1 to 6 carbon atoms, fluorine or chlorine, more preferably a methoxy group, an ethoxy group, a butoxy group, fluorine or chlorine, and further more preferably a methoxy group, an ethoxy group or chlorine.

Preferred examples of the basic carbonates include potassium carbonate and sodium carbonate.

DETAILED DESCRIPTION OF THE INVENTION

The present invention is illustrated in more detail.

In the present invention, the desired compounds represented by formula (II) can be prepared by allowing a 3-amino-4-substituted benzoic acid or an alkali metal salt thereof represented by formula (I) as given above, a basic carbonate such as potassium carbonate or sodium carbonate, and an alkyl halide such as an alkyl chloride or alkyl bromide to react nearly stoichiometrically. The molar ratio of these reactants is preferably from 0.5 to 2.0 mols in the basic carbonate, and from 1.0 to 2.0 mols in the alkyl halide per mol of the 3-amino-4-substituted benzoic acid or the alkali metal salt thereof, and more preferably from 0.9 to 1.2 mol in the basic carbonate, and from 1.0 to 1.3 mol in the alkyl halide per mol of the 3-amino-4-substituted benzoic acid or the alkali metal salt thereof.

As a reaction solvent, there can be used N,N-dimethylformamide, N,N-dimethylacetamide, dimethylsulfoxide and acetone, and more preferably N,N-dimethylformamide and dimethylsulfoxide. The amount of reaction solvent to be used is preferably twice to 10 times, more preferably twice to 5 times, the volume of a 3-amino-4-substituted benzoic acid or an alkali metal salt thereof. Too much reaction solvent results in hindering progress of the reaction, and increasing cost.

Too low reaction temperatures result in disturbing a smooth progress of the reaction, whereas too high temperatures cause by-products to arise. Consequently, the reaction temperature is usually from 20 to 120° C., and preferably from 60 to 100° C.

Further, the order of addition of reactants is important for completing the reaction more favorably. The preferable order of addition comprises the steps of throwing a 3-amino- 4-substituted benzoic acid or an alkali metal salt thereof into a solvent in a vessel, adding a basic carbonate thereto, followed by heating the reaction system at a temperature of 20 to 40° C. for 20 to 60 minutes, preferably 30 to 40 minutes, and adding an alkyl halide thereto. This order provide favorable effect.

According to the process of the present invention, in a compound having two reactive groups of an amino group and a carboxyl group per one molecule, the carboxyl group can selectively react without protecting the other group.

An example of the process for producing the compounds of the present invention is described below.

A 3-amino-4-substituted benzoic acid or an alkali metal salt thereof is added to N,N-dimethylformamide or dimethylsulfoxide. Then potassium carbonate is slowly added to the solution, and the resulting mixture is stirred in the temperature range of from 20 to 40° C. for about 30 min. An alkyl bromide or alkyl chloride is poured into the solution thus obtained. The resulting solution is allowed to react at 80 to 100° C. for 1 to 8 hours, preferably 1 to 4 hours, and then extracted with ethyl acetate after adding water. The ethyl acetate layer separated is concentrated, and then diluted with methanol to precipitate the desired product as crystals. Thus, an alkyl 3-amino-4-substituted benzoate of high purity can be obtained in a high yield.

The present invention is illustrated through the following examples in greater detail. However, these examples are not to be considered as limiting the scope of the present invention.

EXAMPLE 1

Synthesis of Dodecyl 3-Amino-4-chlorobenzoate 17.2 g (0.1 mol) of 3-amino-4-chlorobenzoic acid was added to 50 ml of N,N-dimethylformamide. Then 13.8 g (0.1 mol) of potassium carbonate was added to the solution obtained above, and the resulting mixture was stirred in the temperature range of from 20 to 30° C. for 30 min. 27.4 g (0.11 mol) of dodecyl bromide was poured into the solution thus obtained, and the resulting solution was heated to 80° C., and allowed to react at the temperature for 1 hour. After completing the reaction, 50 ml of ethyl acetate, and 50 ml of water were added to the reaction mixture, and the organic layer was separated, concentrated, diluted with 100 ml of methanol, and then cooled to precipitate crystals. The crystals were separated by filtration, and then dried to obtain 32.3 g (yield 95%) of the desired product. Purity 99% or higher. Melting point 58.3–59.5° C. A result of the elemental analysis of this sample is as follows:

Elemental Analysis

|  | C | H |
|---|---|---|
| Calculated | 67.14 | 8.90 |
| Found | 67.12 | 8.92 |

EXAMPLE 2

Synthesis of Dodecyl 3-Amino-4-chlorobenzoate 17.2 g (0.1 mol) of 3-amino-4-chlorobenzoic acid was added to 50 ml of dimethylsulfoxide.. Then 13.8 g (0.1 mol) of potassium carbonate was added to the solution obtained above, and the resulting mixture was stirred in the temperature range of from 20 to 30° C. for 30 min. 22.5 g (0.11 mol) of dodecyl chloride was poured into the solution thus obtained, and the resulting solution was heated to 100° C., and allowed to react at the temperature for 1 hour. After completing the reaction, 50 ml of ethyl acetate, and 50 ml of water were added to the reaction mixture, and the organic layer obtained was separated, concentrated, diluted with 100 ml of methanol, and then cooled to precipitate crystals. The crystals were separated by filtration, and then dried to obtain 32.3 g (yield 95%) of the desired product. Purity 99% or higher. Melting point 58.0–59.2° C. A result of the elemental analysis of this sample was as follows:

Elemental Analysis

|  | C | H |
|---|---|---|
| Calculated | 67.14 | 8.90 |
| Found | 67.11 | 8.93 |

EXAMPLE 3

Synthesis of Tetradecyl 3-Amino-4-methoxybenzoate 16.7 g (0.1 mol) of 3-amino-4-methoxybenzoic acid was added to 50 ml of N,N-dimethylformamide. Then 13.8 g (0.1 mol) of potassium carbonate was added to the solution obtained above, and the resulting mixture was stirred in the temperature range of from 20 to 30° C. for 30 min. 30.5 g (0.11 mol) of tetradecyl bromide was poured into the solution thus obtained, and the resulting solution was heated to 80° C., and allowed to react at the temperature for 1 hour. After completing the reaction, 50 ml of ethyl acetate, and 50 ml of water were added to the reaction mixture, and the organic layer obtained was separated, concentrated, diluted with 100 ml of methanol, and then cooled to precipitate crystals. The crystals were separated by filtration, and then dried to obtain 33.1 g (yield 91%) of the desired product. Purity 98% or higher. Melting point 54.0–56.0° C. A result of the elemental analysis of this sample was as follows:

Elemental Analysis

|  | C | H |
|---|---|---|
| Calculated | 72.67 | 10.28 |
| Found | 72.65 | 10.29 |

According to the present invention in the similar manner as in Examples 1 to 3, dodecyloxycarbonylethyl 3-amino-4-chlorobenzoates having a dodecyloxycarbonylethyl group as a substituted alkyl group can be prepared by a simple procedure.

According to the present invention, alkyl 3-amino-4-substituted benzoates of high purity can be efficiently prepared in high yields by simple procedure.

While the invention has been described in detail and with reference to specific examples thereof, it will be apparent to one skilled in the art that various changes and modifications can be made therein without departing from the spirit and scope thereof.

What is claimed is:

1. A process for producing an alkyl 3-amino-4-substituted benzoate represented by the following formula (II), in which a 3-amino-4-substituted benzoic acid or an alkali metal salt thereof represented by the following formula (I) is allowed to react with an alkyl halide in the presence of a basic carbonate:

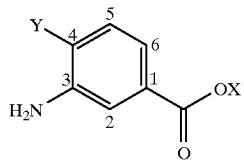
(I)

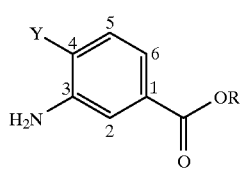
(II)

wherein R represents an alkyl group, X represents an alkali metal atom or a hydrogen atom, and Y represents an alkoxy group or a halogen atom,
  wherein the amount of the basic carbonate is from 0.5 to 2.0 mols per mol of the 3-amino-4-substituted benzoic acid or the alkali metal salt thereof.
2. The process for producing an alkyl 3-amino-4-substituted benzoate as claimed in claim 1, in which X represents a hydrogen atom, and Y represents a chlorine atom.
3. The process for producing an alkyl 3-amino-4-substituted benzoate as claimed in claim 1, in which said alkyl group is an unsubstituted or substituted alkyl group having 6 to 18 carbon atoms.
4. The process for producing an alkyl 3-amino-4-substituted benzoate as claimed in claim 1, in which said alkyl group is selected from the group consisting of an aliphatic alkyl group, a cyclic alkyl group, an alkoxycarbonylalkyl group and an alkylaminocarbonylalkyl group.
5. The process for producing an alkyl 3-amino-4-substituted benzoate as claimed in claim 1, in which said alkyl halide is selected from the group consisting of alkyl bromides and alkyl chlorides.
6. The process for producing an alkyl 3-amino-4-substituted benzoate as claimed in claim 1, in which said basic carbonate is selected from the group consisting of potassium carbonate and sodium carbonate.
7. The process for producing an alkyl 3-amino-4-substituted benzoate as claimed in claim 1, in which the amount of the basic carbonate is from 0.9 to 1.2 mol per mol of the 3-amino- 4-substituted benzoic acid or the alkali metal salt thereof.
8. The process for producing an alkyl 3-amino-4-substituted benzoate as claimed in claim 1, in which the amount of the alkyl halide is from 1.0 to 2.0 mols per mol of the 3-amino-4-substituted benzoic acid or the alkali metal salt thereof.
9. The process for producing an alkyl 3-amino-4-substituted benzoate as claimed in claim 7, in which the amount of the alkyl halide is from 1.0 to 1.3 mol per mol of the 3-amino-4-substituted benzoic acid or the alkali metal salt thereof.

* * * * *